(12) United States Patent
Powell (10) Patent No.: US 9,347,014 B2
(45) Date of Patent: May 24, 2016

(54) METHODS AND SYSTEMS FOR GENERATING ALDEHYDES FROM ORGANIC SEED OILS

(71) Applicant: GFO OIL LLC, Sheridan, CO (US)

(72) Inventor: Wayne J. Powell, Centennial, CA (US)

(73) Assignee: GFO OIL LLC, Sheridan, CO (US)

( * ) Notice: Subject to any disclaimer, the term of this patent is extended or adjusted under 35 U.S.C. 154(b) by 0 days.

(21) Appl. No.: 14/244,243

(22) Filed: Apr. 3, 2014

(65) Prior Publication Data

US 2014/0303056 A1 Oct. 9, 2014

Related U.S. Application Data

(60) Provisional application No. 61/807,936, filed on Apr. 3, 2013.

(51) Int. Cl.
*C25B 3/00* (2006.01)
*C10M 129/24* (2006.01)
*C10L 1/185* (2006.01)
*C10M 105/20* (2006.01)

(52) U.S. Cl.
CPC ............ *C10M 129/24* (2013.01); *C10L 1/1857* (2013.01); *C10M 105/20* (2013.01); *C10L 2200/0484* (2013.01); *C10L 2290/38* (2013.01); *C10M 2207/08* (2013.01); *C10N 2230/50* (2013.01); *C10N 2270/00* (2013.01)

(58) Field of Classification Search
CPC ................. C25B 3/00; C25B 3/02; C25B 3/04
USPC ................... 205/413, 440, 441, 448, 462, 695
See application file for complete search history.

(56) References Cited

U.S. PATENT DOCUMENTS

| | | | |
|---|---|---|---|
| 3,112,329 A | 11/1963 | Pryde et al. | |
| 3,349,106 A | 10/1967 | Moore | |
| 3,504,038 A | 3/1970 | Beal et al. | |
| 3,941,685 A * | 3/1976 | Singewald et al. | 209/9 |
| 5,766,272 A | 6/1998 | Lozzi | |
| 6,207,624 B1 | 3/2001 | Stachew et al. | |
| 6,514,298 B2 | 2/2003 | Haji et al. | |
| 6,768,029 B1 | 7/2004 | Khan et al. | |

(Continued)

FOREIGN PATENT DOCUMENTS

| | | |
|---|---|---|
| AU | 754495 | 11/2002 |
| EP | 1681338 | 7/2006 |

(Continued)

OTHER PUBLICATIONS

Brands et al., "Electrostatic Separation", Ullmann's Encyclopedia of Industrial Chemistry (© no month, 2012), vol. 12, pp. 423-441.*

(Continued)

*Primary Examiner* — Edna Wong
(74) *Attorney, Agent, or Firm* — Fish & Tsang LLP (57) ABSTRACT

Methods for generating aldehyde-containing compounds in organic seed oils utilizing ozone and direct current without the use of added electrolytes and reducing compounds are disclosed, as are compositions generated by such methods. The reactions can be performed efficiently at ambient temperatures and pressures. These compositions have particular utility as additives to fuels and lubricating oils derived from petrochemical sources.

9 Claims, 9 Drawing Sheets

(56) References Cited

U.S. PATENT DOCUMENTS

| | | | |
|---|---|---|---|
| 7,074,872 | B2 | 7/2006 | Khan et al. |
| 7,497,939 | B2 | 3/2009 | Matsumura et al. |
| 8,329,942 | B2 | 12/2012 | Kondo et al. |
| 8,394,966 | B2 | 3/2013 | Almstead et al. |
| 2001/0005957 | A1 | 7/2001 | Haji et al. |
| 2004/0108219 | A1* | 6/2004 | Matsumura et al. .......... 205/441 |
| 2005/0010069 | A1 | 1/2005 | Fitchett et al. |
| 2005/0120621 | A1* | 6/2005 | Lawson et al. ................ 44/388 |
| 2005/0262760 | A1* | 12/2005 | Lawson et al. ................ 44/388 |
| 2006/0074129 | A1 | 4/2006 | Mirabal et al. |

FOREIGN PATENT DOCUMENTS

| | | | |
|---|---|---|---|
| EP | 2386535 | 11/2011 | |
| EP | 2644684 | 10/2013 | |
| KR | 1020110124765 | 11/2011 | |
| WO | WO 2006128881 A1 * | 12/2006 | ............... C10L 1/02 |
| WO | 2010/084053 | 7/2010 | |
| WO | 2010/091069 | 8/2010 | |
| WO | 2012/168770 | 12/2012 | |

OTHER PUBLICATIONS

Badent et al., "Behaviour of Rape-Seed-Oils Under Impulse Voltages", Electrical Insulation and Dielectric Phenomena, 1999 Annual Report Conference on (no month, 1999), vol. 2. IEEE, pp. 638-641.*

Badent et al., "Behaviour of Rape-Seed-Oils Under Impulse Voltages", 1999 Conference on Electrical Insulation and Dielectric Phenomena (1999), IEEE, vol. 2, pp. 638-641.*

Soriano Jr., N. U. et al., "Electrolytic cleavage of 1,2,4-trioxolanes of sunflower oil methyl esters", Electrochimica Act, vol. 50, 2005, pp. 1131-1137.

Pryde, E.H. et al., "Ozonization of Soybean Oil. The Preparation and Some Properties of Aldehyde Oils", The Journal of the American Oil Chemists' Society, vol. 38, Jul. 1961, pp. 375-379.

* cited by examiner

METHODS AND SYSTEMS FOR GENERATING ALDEHYDES FROM ORGANIC SEED OILS

This application claims the benefit of priority to U.S. Provisional Application No. 61/807,936 filed on Apr. 3, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is chemical modification of organic seed oils to produce aldehydes.

BACKGROUND

The following description includes information that may be useful in understanding the present invention. It is not an admission that any of the information provided herein is prior art or relevant to the presently claimed invention, or that any publication specifically or implicitly referenced is prior art.

As renewable sources, vegetable seed oils are an attractive and environmentally friendly source of long chain hydrocarbon compounds. As a biological source, however, the compounds represented in such vegetable seed oils, while diverse, may not include species that are suited for a desired purpose. Towards that end a variety of methods have been developed to alter the composition of vegetable seed oils. Ideally, such methods should produce desirable compounds, for example oxygenated species such as aldehydes, in useful quantities and in a scalable fashion, and preferably not involve the addition of compounds that would be retained in the product mixture.

Soriano Jr. et al (Electrochemica Acta 50:1131-1137 (2005)) reported production of oxygenated species in sunflower oil via production of trioxilanes by treatment with ozone and low voltage electrolytic reduction. This process, however, required the addition of soluble metal salt electrolytes and alcohol and carboxylic acid proton donors. Similarly, U.S. Pat. No. 7,497,939 (to Matsumura et al) discloses a method for producing oxygenated species from vegetable oil by first esterifying the vegetable oil by treatment with an alcohol and a strong base, then reacting with ozone and performing an electrochemical reduction at low voltage and in the presence of a soluble metal salt electrolyte and organic acid and/or alcohol proton donors. U.S. Pat. No. 6,768,029 (to Khan et al) teaches a method for producing oxygen containing species from various naturally occurring oils by first dissolving the oil in an alcohol and treating with ozone, then performing a chemical reduction using an added reducing sugar (for example, glucose). All of these approaches, however, require the addition of metal salts, organic acids, and/or alcohols that often need to be removed via additional processing steps prior to use of the modified vegetable oil. Such post-reaction processing is a significant impediment to scale-up and commercialization of such methods. The reliance on ozone, which has a permissible exposure limit of 0.1 μmol/mol under current OSHA regulations can also complicate the implementation of such processes.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for a scalable method for generating oxygenated and other useful molecular species from vegetable oils.

SUMMARY OF THE INVENTION

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which aldehyde containing compounds are generated from organic seed oils by exposure to direct current in the presence of an electrical field and without the use of added electrolytes or reducing agents. Following such treatment, the modified organic seed oil compositions have particular utility as additives in fuels and lubricating oils.

One embodiment of the inventive concept is a method for producing a petroleum product additive by placing at least two electrodes in a vegetable oil and applying a fixed polarity (i.e. DC) electrical potential across the electrodes of at least 3 $kV/cm^2$. Suitable vegetable oils include canola (rapeseed) oil, olive oil, and sunflower oil with a oleic acid content of at least 70%. In some embodiments the magnitude of the electrical potential is varied over time during the process. Suitable electrodes include brass, stainless steel, and copper electrode. In some embodiments both electrodes have the same composition, whereas in other embodiments the electrodes have different compositions. The gap between the electrodes ranges from 5 mm to 100 mm, and is preferably about 40 mm. The vegetable oil is exposed to the electrical potential for a time sufficient to generate the desired amount of product compounds, for example from 8 hours to 48 hours. In some embodiments of the inventive concept ozone is introduced to the vegetable oil during all or part of the reaction, for example at a rate of 0.5 g per hour.

Another embodiment of the inventive concept is a petroleum product additive that includes an oxygenated hydrocarbon (such as an aldehyde) produced by exposing a vegetable oil to at least two electrodes and applying an electrical potential of fixed polarity to the electrodes. The magnitude of the potential is at least 3 kV per cm of distance between the electrodes. The resulting petroleum product additive has less than 1% (v/v) of a chemical reductant, for example an alcohol, and less than 100 ppm of an organic soluble electrolyte (for example an organic metal salt).

Another embodiment of the inventive concept is an augmented lubricating oil, which includes a base (i.e. not augmented) lubricating oil to which has been added an oxygenated hydrocarbon. The augmented hydrocarbon has been produced by exposing at least two electrodes to a vegetable oil and applying an electrical potential to the electrodes. In such embodiments the applied electrical potential has a fixed polarity and a magnitude of at least 3 kV per cm of distance between the electrodes.

Still another embodiment of the inventive concept is an augmented fuel, which includes a base (i.e. not augmented) fuel to which has been added an oxygenated hydrocarbon. The augmented hydrocarbon has been produced by exposing at least two electrodes to a vegetable oil and applying an electrical potential to the electrodes. In such embodiments the applied electrical potential has a fixed polarity and a magnitude of at least 3 kV per cm of distance between the electrodes.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 2A to FIG. 2E show typical GCMS results of the products of treatment of canola oil using various combinations of reaction conditions.

FIG. 3A to FIG. 3D show typical GCMS results of the products of treatment of canola oil with ozone and applied voltage in the presence of copper for different periods of time.

FIG. 6A and FIG. 6B schematically depict different reactor designs.

DETAILED DESCRIPTION

Methods for treating vegetable oils to generate oxygenated hydrocarbons (such as aldehydes) have been developed that utilize ozone and current applied through a pair of electrodes, without the need for adding an electrolyte and/or a chemical reductant to the reaction mixture. It was also found that vegetable oils treated in such a manner were effective as additives or augmenting agents for lubricating oils and for fuels used in engines, reducing harmful emissions and improving engine performance.

It should be appreciated that such methods are surprisingly scalable and environmentally benign, as processing of the modified vegetable oil product to remove residual electrolytes and chemical reductant (typically organic acid and/or alcohols) is unnecessary. In addition, the disclosed methods provide a product generated from a renewable resource (i.e. a vegetable oil) that significantly reduces the emission of harmful pollutants from internal combustion engines.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter provides systems and methods for producing aldehydes (ex: hexanal and nonanal) from organic oils, for example organic seed oils. Suitable organic oils include rapeseed (i.e. canola) oil, olive oil, sunflower oil, coconut oil, corn oil, cottonseed oil, palm oil, peanut oil, safflower oil, sesame oil, soybean oil, mustard oil, almond oil, beech nut oil, cashew oil, hazelnut oil, macadamia nut oil, monjogo oil, pecan oil, pine nut oil pistachio oil, and walnut oil. In a preferred embodiment canola oil, olive oil, and sunflower oil with an oleic acid content of at least 70% is utilized as a starting material. In some embodiments a mixture of different oil types is used as a starting material. Such vegetable oils can be provided as fresh, unused materials, or can be provided as materials that have been used in other processes (for example, cooking).

Methods of the inventive concept can utilize ozone, copper (for example, copper plates or electrodes), and/or an applied electromagnetic field (for example, a voltage potential applied to two or more electrodes) to generate aldehydes from compounds found in the vegetable oil starting material. Unlike prior art methods, these processes take place without the addition of electrolytes (such as organic soluble metal salts) or chemical reducing agents (such as organic acids and/or alcohols), which require additional processing steps to remove from the product, to the starting material. As a result, vegetable oils thus treated (i.e. modified vegetable oils) have low (less than 100 ppm) to undetectable concentrations of electrolytes and low (less than 1%) to undetectable concentrations of chemical reducing agents. Without wishing to be bound by theory, the inventors believe that at least a portion of the process is a result of ozonolysis of alkene compounds that occur in the starting material, as shown in Formula I.

Formula I

Ozonide

Carbonyl Products

Surprisingly, however, inventors have found that, while the addition of ozone to the vegetable oil during the process is preferred and improves the yield of oxygenated hydrocarbon products such products are also generated when such ozone is not provided. The inventors contemplate that methods of the inventive concept that incorporate the use of ozone can do so utilizing substantially less ozone than is utilized in prior art methods.

In a typical method of the inventive concept, two or more electrodes are inserted into a container of a suitable vegetable oil. Such electrodes can be constructed of any suitably conductive material, such as metal (i.e. copper, brass, stainless steel, aluminum, etc.), conductive polymer, carbon (i.e. graphite), or a combination thereof. In a preferred embodiment the electrodes made, at least in part of copper. In embodiments that do not utilize copper as an electrode component, copper metal can be added to the vegetable oil in the form of plates, rods, granules, pellets, discs, powder, or any suitable form. The electrodes are separated by a gap, which can range from about 5 mm to about 100 mm. In a preferred embodiment the gap or space between the electrodes is about 40 mm.

Figure 1:
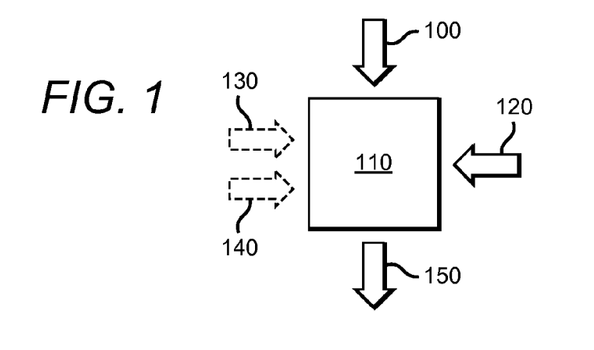
FIG. 1 schematically depicts an exemplary method of the inventive concept.

A typical method of the inventive concept is illustrated schematically in FIG. 1. A vegetable oil 100 is provided to a reactor 110, along with an electrical potential 120 (for example, a potential applied to a pair of electrodes within the reactor). Optionally, ozone 130 and/or copper 140 can be supplied to the reactor during the reaction. In a preferred embodiment of the inventive concept, both ozone and copper are supplied to the reactor. In some embodiments, copper 140 can be supplied through the use of copper electrodes used to supply the electrical potential 120. Similarly, ozone 130 can be supplied through the use of an ozone generator and an ozone supply line that enter the reactor 110. During the reaction, oxygenated hydrocarbon compounds (for example an aldehyde) are generated within the reactor 110, from which a treated or modified vegetable oil 150 that includes such oxygenated hydrocarbons can be collected.

It is contemplated that the composition of the resulting product molecules (for example, molecular weight distribution) can be controlled by modulation of process variables such as voltage, ozone, temperature, and treatment time. In some instances, for example producing a product with a desired lubricity, it can be desirable to control such conditions to favor the production of shorter carbon chains. Applicant has found that this can be achieved by controlling the amount of ozone supplied to the reaction, with increasing ozone favoring the production of products with enhanced lubricity.

In methods of the inventive concept that utilize an electromagnetic field, an electrical potential is applied via electrodes such as those described above. In a preferred embodiment of the inventive concept this potential is applied as direct current, such that the polarity of the electrodes does not change during the process. Such electrical potentials can range from 1 kV per cm of distance between the electrodes to 10 kV per cm of distance between the electrodes or more, and can be adjusted to accommodate different electrode materials and/or configurations. For example, the electrical potential applied to a pair of electrodes can be 3 kV per cm of distance between electrodes in a first configuration, and can be modified as size or orientation of the electrodes changes (for example, in adjusting the scale of the reaction). In a preferred embodiment of the inventive concept the electrical potential is about 4 kV per cm of distance between the electrodes. Such a large electrical potential generates an electromagnetic field between the electrodes, and without wishing to be bound by theory the inventors believe that this field may serve to at least partially align or organize molecular oxygen and/or ozone in the vegetable oil and thereby affect its reactivity with vegetable oil components, possibly at or near copper surfaces. As such, it should be appreciated that the spacing between electrodes and the magnitude of the applied potential can be a function of the scale at which the method is being applied. For example, in large scale applications it may be desirable to utilize a relatively large gap between the electrodes (i.e. 100 mm or greater), which can require higher electrical potentials (i.e. 10 kV/cm$^2$ or higher) to attain the desired effect. In some embodiments of the inventive concept the potential between the electrodes is essentially constant throughout the reaction. In other embodiments of the inventive concept the magnitude of the electrical potential can be varied during the reaction. In such embodiments the electrical potential can trend in a single direction (i.e. increase or decrease) as the reaction progresses. In other such embodiments the electrical potential can be varied in a rhythmic or pulsatile manner, for example in a waveform. Such pulses of electrical potential can be provided in a manner (for example, at a frequency or pattern of frequencies) that generates a resonance.

In methods of the inventive concept that utilize ozone, ozone can be supplied as a gas that is introduced into the volume of vegetable oil so as to provide an extended contact time, for example through an outlet or diffuser or similar device located in a lower part of the container in which the reaction is performed. Such an outlet or diffuser can be arranged to direct the flow of ozone so that it passes through the gap between a pair of electrodes or plates. In some embodiments ozone may be introduced via a venturi device in order to provide the gas as small bubbles that improve mixing and dissolution of the ozone. Ozone can be introduced at a rate ranging from 0.1 g per hour to 10 g per hour. In preferred embodiments ozone is introduced at a rate of about 0.5 g per hour. It should be appreciated, however, that the rate and manner in which ozone is introduced can be adjusted to the scale of the reaction. In some embodiments ozone can be produced at the site of the reaction, for example by a corona discharge and/or a UV irradiation device that utilizes molecular oxygen (i.e. $O_2$) from the ambient atmosphere to produce ozone. In such an embodiment, ozone can be introduced to the reaction as a mixture of ozone and ambient air, at concentrations ranging from 1% to 10% (v/v) ozone. In a preferred embodiment, ozone is supplied by a corona discharge device at a concentration of from 3% to 6% (v/v) in ambient air. In still other embodiments unreacted ozone can be captured and re-used.

Figure 2A:
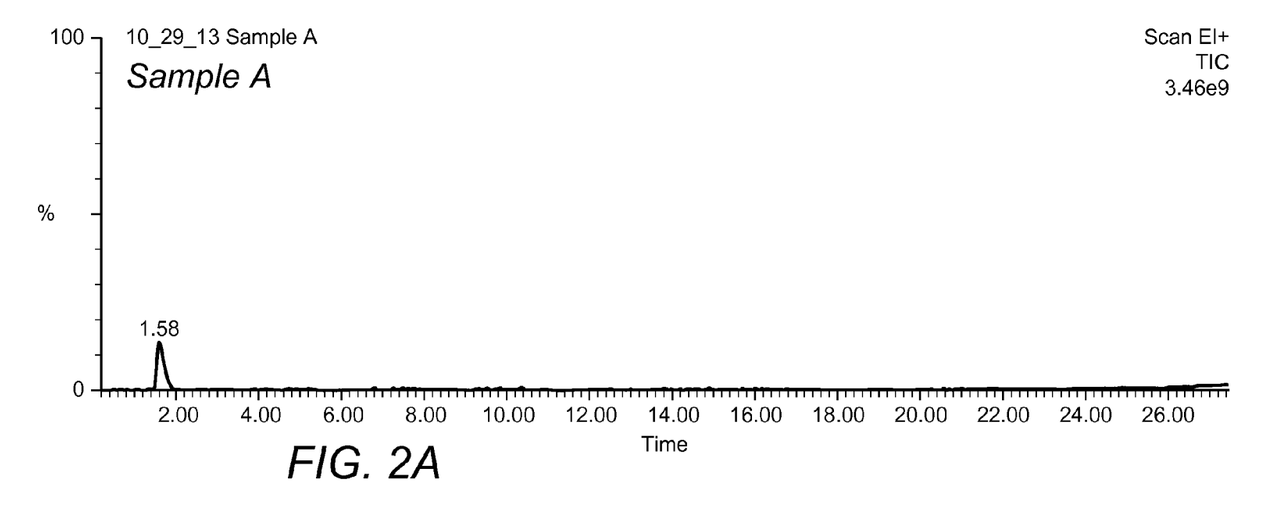
FIG. 2A shows results from untreated canola oil.
Figure 2B:
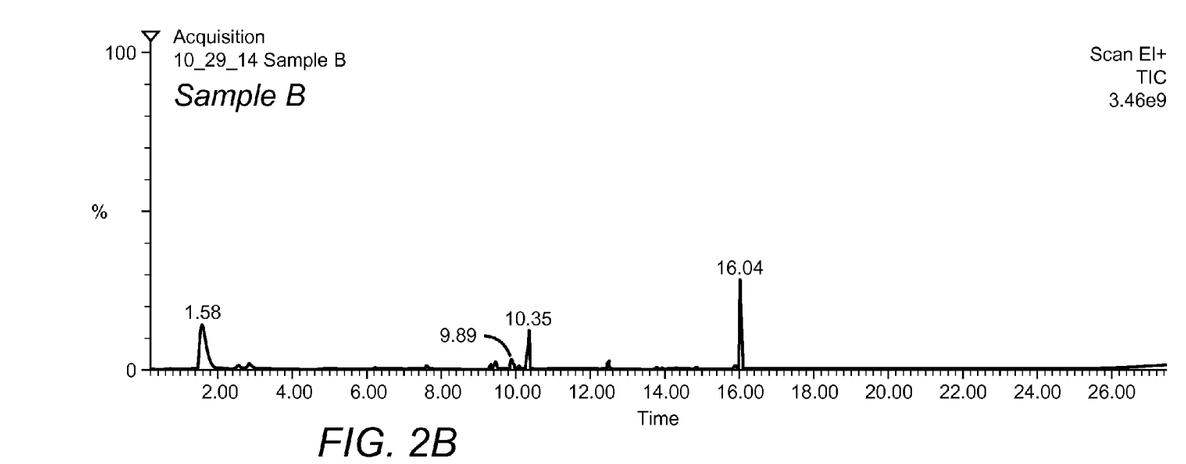
FIG. 2B shows results from canola oil treated with ozone and an applied voltage, in the absence of copper.
Figure 2C:
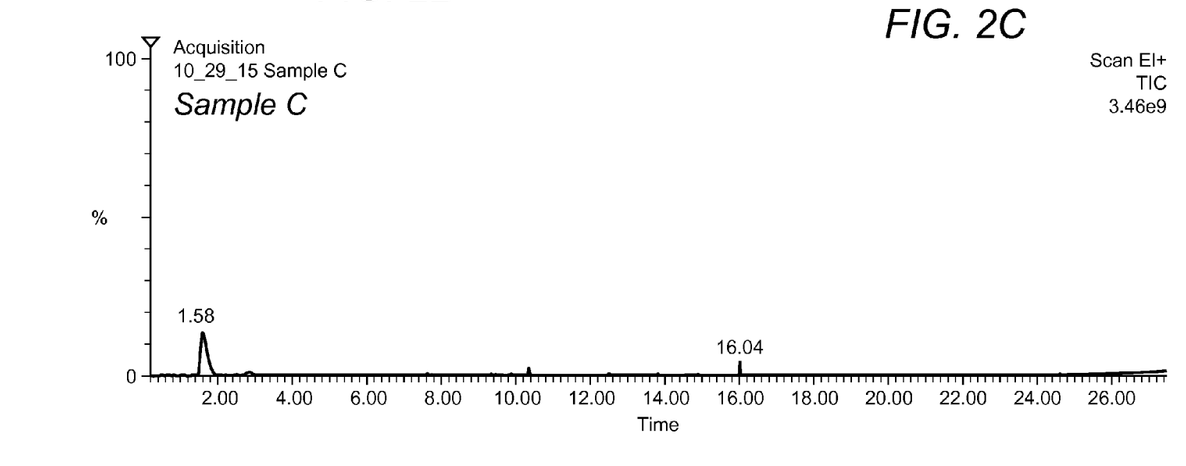
FIG. 2C shows results from canola oil treated with voltage and exposed to copper, in the absence of ozone.
Figure 2D:
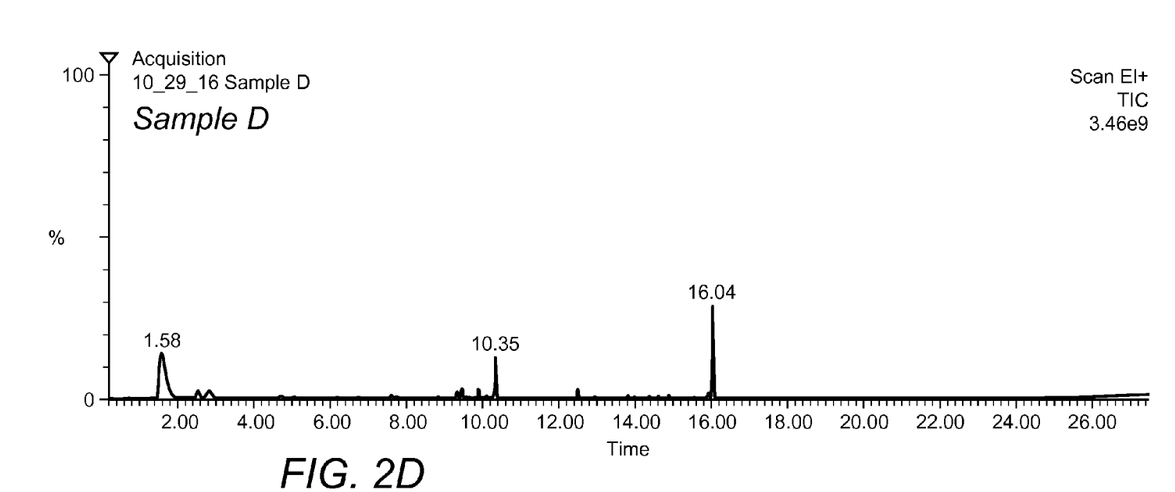
FIG. 2D shows results from canola oil treated with ozone and exposed to copper, in the absence of applied voltage.
Figure 2E:
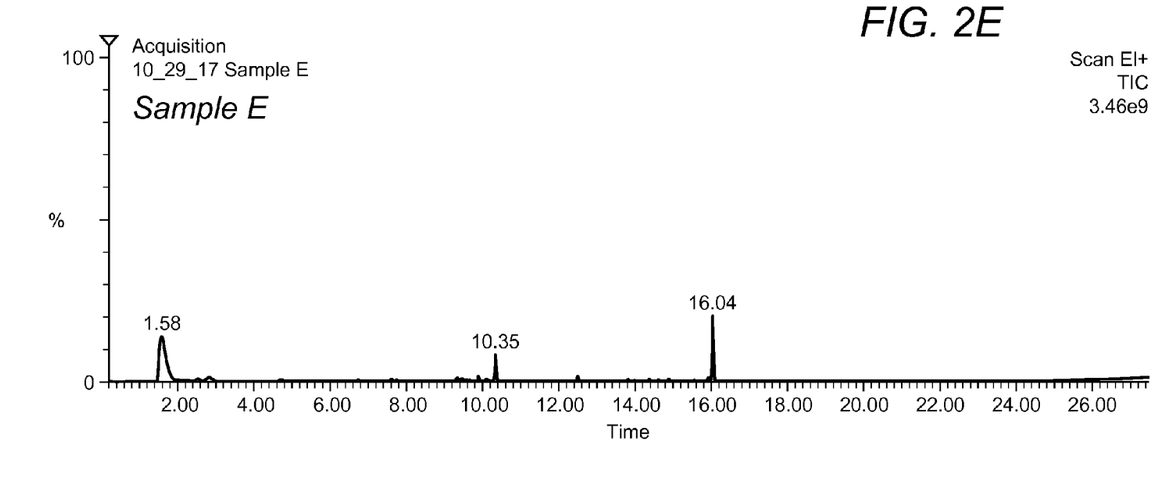
FIG. 2E shows results from canola oil treated with ozone and applied voltage in the presence of copper.
Figure 4:
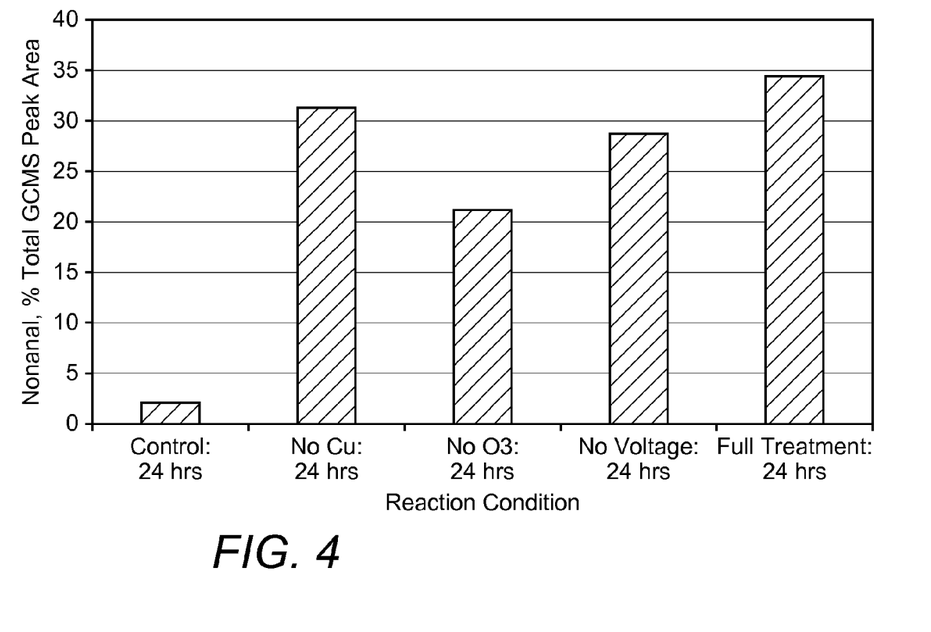
FIG. 4 shows the effect of different reaction conditions on the generation of nonanal in canola oil.

In preferred embodiments of the inventive concept, aldehydes are generated in vegetable oil by the application of a large (i.e. >1 $kV/cm^2$) electrical potential applied to copper-containing electrodes as ozone is applied. Surprisingly, however, the inventors have found that aldehydes (notably hexanal and nonanal) can be produced by alternative methods of the inventive concept that lack certain of these elements, as shown in FIG. 2A to FIG. 2E. FIG. 2A shows GCMS results of canola oil that has not been treated (beyond exposure to room air for 24 hours), and which shows no apparent aldehyde content. However, as shown in FIG. 2B, introduction of ozone in the presence of a 4 kV per cm of distance between the electrodes electrical potential and in the absence of copper for 24 hours can produce numerous previously unobserved compounds, including aldehydes. Surprisingly, as shown in FIG. 2C, similar compounds are generated by the application of a 4 kV per cm of distance between the electrodes electrical potential using copper electrodes without the addition of ozone. Similar compounds are also generated by the application of ozone in the presence of copper and without the application of an electrical potential, as shown in FIG. 2D. The results of the application of ozone in the presence of copper electrodes and a 4 kV per cm of distance between the electrodes electrical potential to canola oil are shown in FIG. 2E. As shown in FIG. 4, which shows the percentage of total peak area represented by nonanal in the data of FIG. 2A through 2E, while all of these processes impact the composition of the treated canola oil, the combined use of copper, ozone, and electrical potential (i.e. full treatment) provides the greatest effect. In some embodiments of the inventive concept any one of these processes can be suitable.

Surprisingly, such aldehydes are produced on application of the electrical potential without the addition of electrolytes to the vegetable oil, for example soluble metal salts, which is typically found in the prior art. As a result, such electrolytes are not found in significant quantities (i.e. equal to or less than 100 ppm) in the treated vegetable oil product. Similarly, such aldehydes are produced without the need to add chemical reductants, such as alcohols, organic acids, or combinations of alcohols and organic acids, to the vegetable oil. Such chemical reductants are typically added at concentrations of up to 50% (v/v) in the prior art. As a result, a treated vegetable oil product does not contain significant quantities (i.e. equal to or less than 1% (v/v)) of such added chemical reductants. As a result, additional processing of treated vegetable oil to remove or reduce such electrolytes and/or chemical reductants is unnecessary. This advantageously reduces waste associated with processes of the inventive concept and permits use of a treated vegetable oil (for example, as an engine oil or fuel additive) without the need for expensive and time consuming intervening processing steps.

Figure 3A:
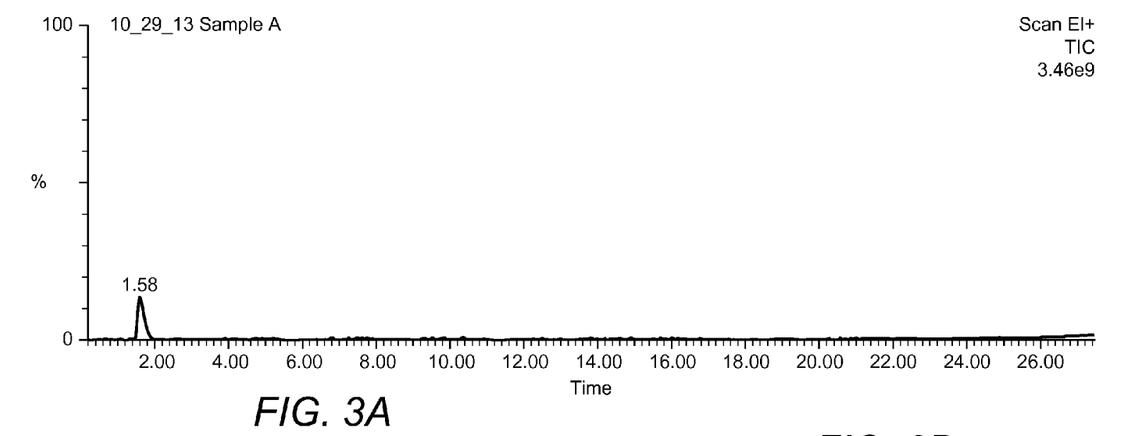
FIG. 3A shows results from canola oil prior to the initiation of treatment.
Figure 3B:
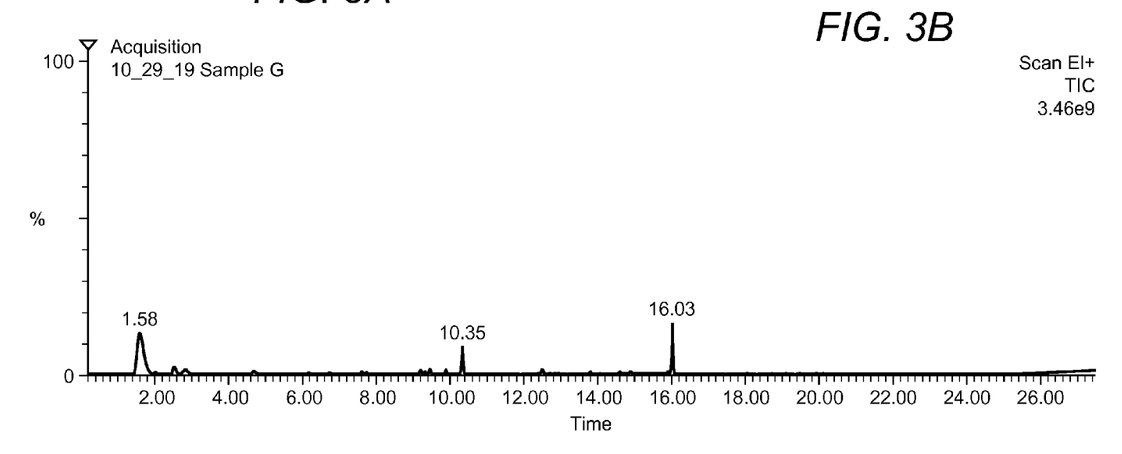
FIG. 3B shows results from canola oil after 8 hours of treatment.
Figure 3C:
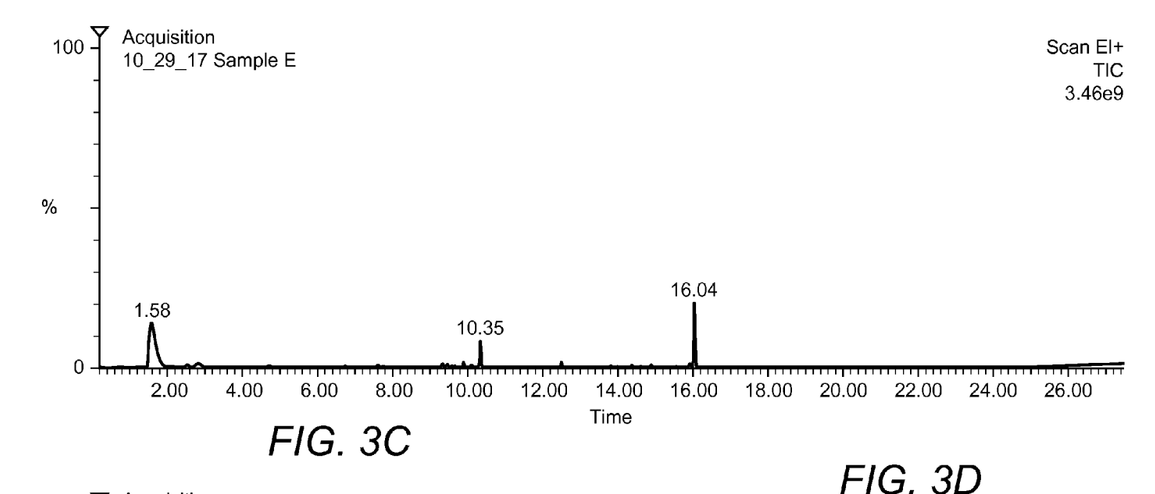
FIG. 3C shows results from canola oil after 24 hours of treatment.
Figure 3D:
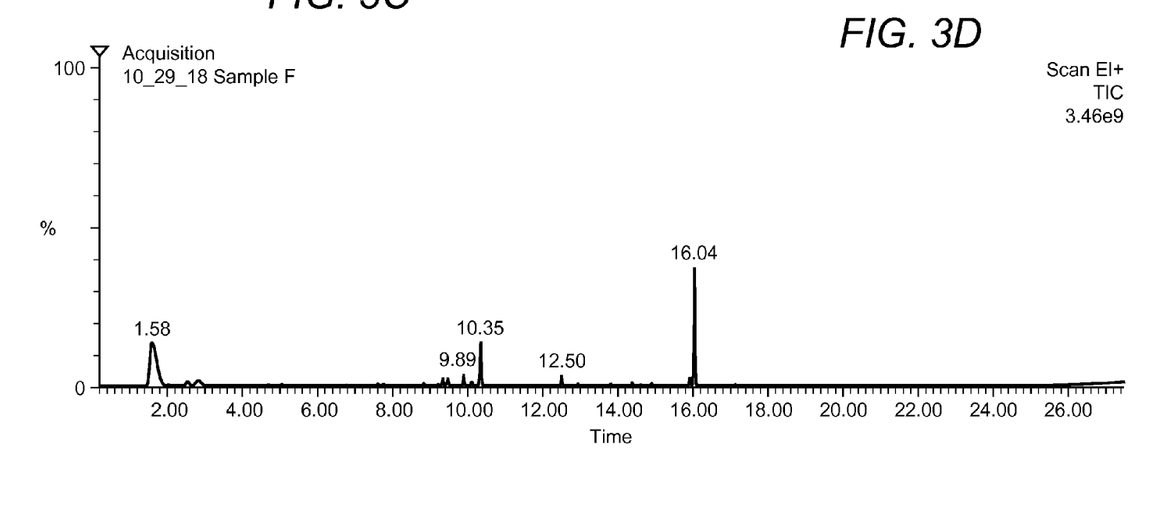
FIG. 3D shows results from canola oil after 48 hours of treatment.
Figure 5:
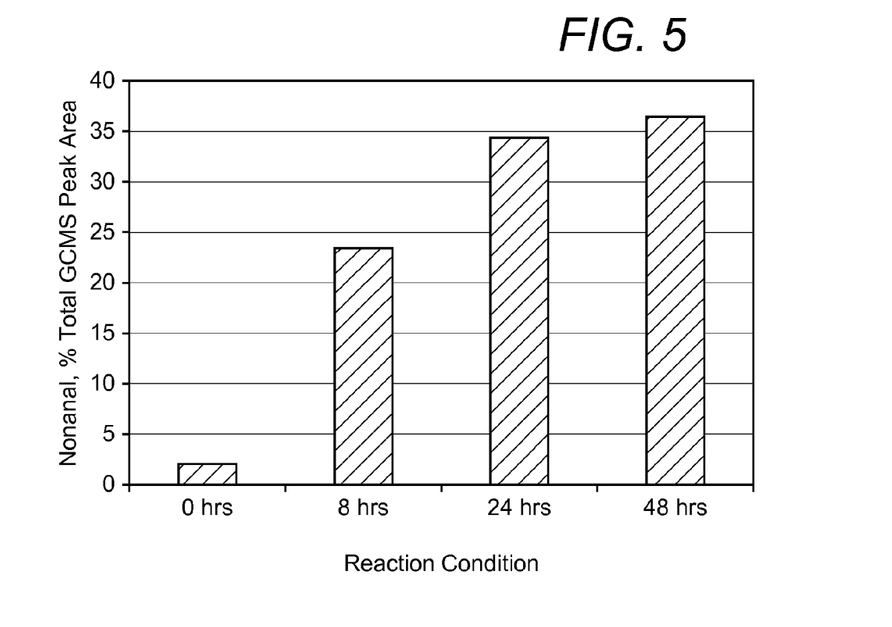
FIG. 5 shows the time course of the generation of nonanal when canola is treated by a method of the inventive concept.

Vegetable oils can be subjected to the conditions of the inventive concept for any period of time necessary to generate the desired quantity or concentration of oxygenated hydrocarbons. Suitable time periods typically range from 8 hours to 48 hours or more. In a preferred embodiment of the inventive concept the vegetable oil is treated for about 24 hours. A typical time course for the reaction of canola oil by treatment with ozone in the presence of copper electrodes to which a 4 kV per cm of distance between the electrodes electrical potential is applied is shown in FIG. 3A to FIG. 3D. FIG. 3A shows GCMS data from untreated (beyond exposure to ambient air for 24 hours) canola oil, FIGS. 3B, 3C, and 3D show similar data from canola oil treated for 8 hours, 24 hours, and 48 hours, respectively. It should be noted that the color changes significantly during treatment, and such a color or absorbance change can be used as an indicator of when the reaction has reached a desired point. FIG. 5 shows how the percentage of total GCMS peak area represented by nonanal changes with time.

Figure 6A:
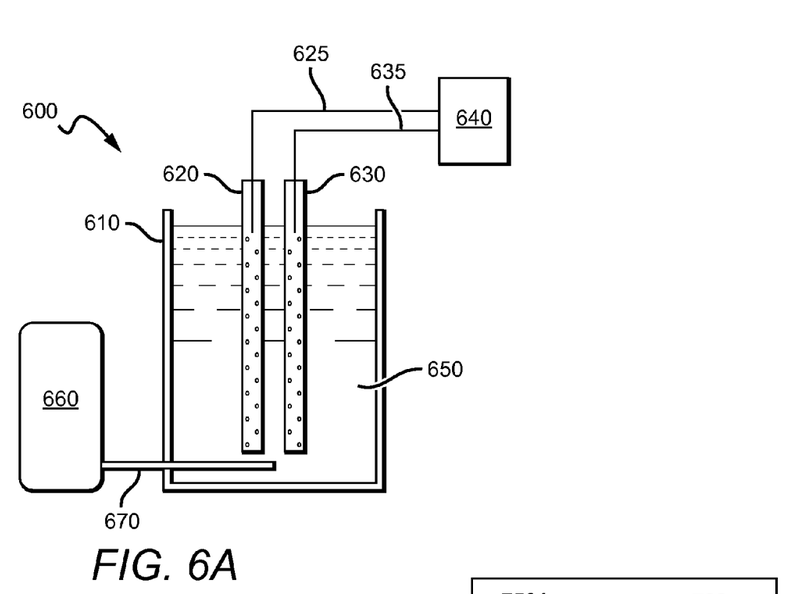
FIG. 6A schematically depicts a batch reactor.

The processes described above can be implemented in a batch reactor, as shown schematically in FIG. 6A. In such a reactor 600, a container or vessel 610 is provided, along with a pair of electrodes 620, 630 that have connections 625, 635 to a power supply 640. The power supply 640, which can be a battery, a generator, an alternator, or a transformer connected to local mains power supplies, is configured to provide a potential of at least 1 kV per cm of distance between the electrodes across the electrodes 620, 630. In use, the electrodes 620, 630 are at least partially submerged in a volume of suitable vegetable oil 650. Ozone is supplied to the reactor 600 by an ozone source 660, for example a corona discharge device, and directed via an ozone supply line 670 into the vessel 610. The outlet of the ozone supply line 670 can be arranged to direct the flow of ozone between the electrodes 620, 630. Such a reactor 600 can also include additional features, such as a diffuser or venturi connected to the ozone supply line 670, a mixing device, and a temperature control device (for example, a temperature control loop in thermal communication with the volume of oil 650). Such a reactor can be used at ambient (i.e. 20° C. to 25° C.) temperatures, which can increase to about 40° C. during use. In such a batch reactor 600 a single volume of vegetable oil is treated for a specified period of time to produce a single volume of modified vegetable oil.

Figure 6B:
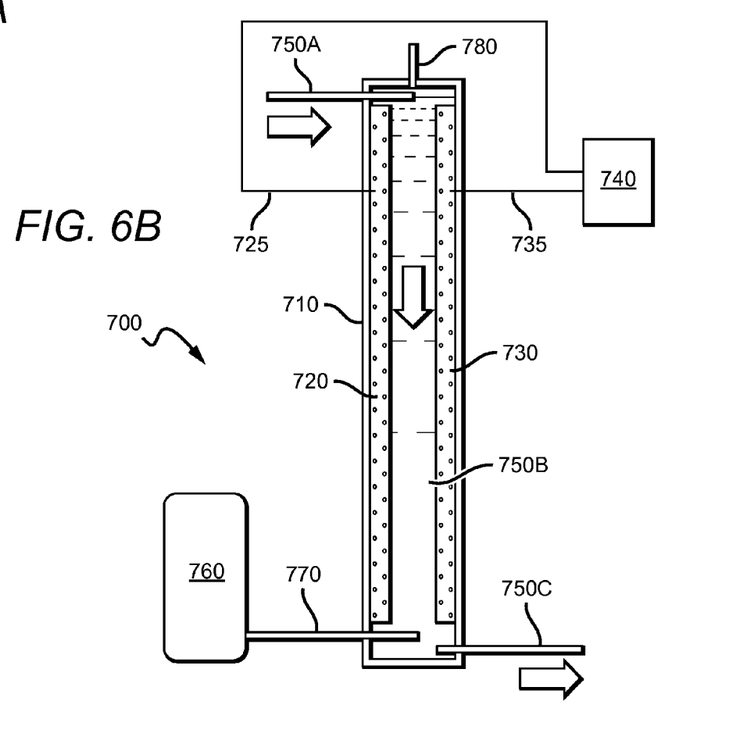
FIG. 6B schematically depicts a flow reactor.

It should be appreciated, however, that the reaction can be performed in a continuous flow fashion, as depicted schematically in FIG. 6B. For example, a continuous flow reactor 700 can be provided with vegetable oil as a flowing volume that enters through an inlet 750A, flows through 750 B the flow reactor 700, and exits through an outlet 750C as a flow of modified vegetable oil. As it moves through the flow reactor the flow of vegetable oil 750B moves between a pair of copper electrodes 720, 730 that have connections 725, 735 to a power supply 740. The power supply can be a battery, a generator, an alternator, or a transformer connected to local mains power supply, and can be configured to provide a potential of at least 1 kV per cm of distance between the electrodes across the electrodes 720, 730. Ozone can be provided by an ozone supply 760, for example a corona discharge device, and introduced to the flow reactor 710 via an ozone supply line 770. In preferred embodiments, the ozone supply line is positioned such that the ozone gas thus introduced moves through the flow reactor 700 in the opposite direction of the flow of vegetable oil 750B. Excess or unreacted ozone can be removed from the reactor via an ozone vent 780. The respective flow rate of the vegetable oil, the application rate of the ozone, and the magnitude of the electrical potential can be selected to produce a suitably modified vegetable oil at the outlet of the reactor. Such a reactor can be configured as an extended or coiled tube or cylinder, with the electrode pair affixed to the inner surface.

Inventors have also discovered that the modified vegetable oils resulting from treatment by the processes described above have utility as additives to lubricating/motor oils and as additives to motor fuels. The resultant aldehydes from this process can be used as an engine treatment to provide a noticeable boost in horsepower and performance, or used to clean carbon residue inside the engine by adding small amounts to the engine's oil. When used as a motor oil additive, the modified vegetable oil can be added at 1% (v/v) to 10% (v/v) of the volume of the motor oil to produce an augmented motor oil. In some embodiments the modified vegetable oil can be added at 3% (v/v) to 9% (v/v) of the volume of the motor oil to produce an augmented motor oil. In a preferred embodiment of the inventive concept the modified vegetable oil is added at about 3% (v/v) of the volume of the motor oil to produce an augmented motor oil.

Figure 7:
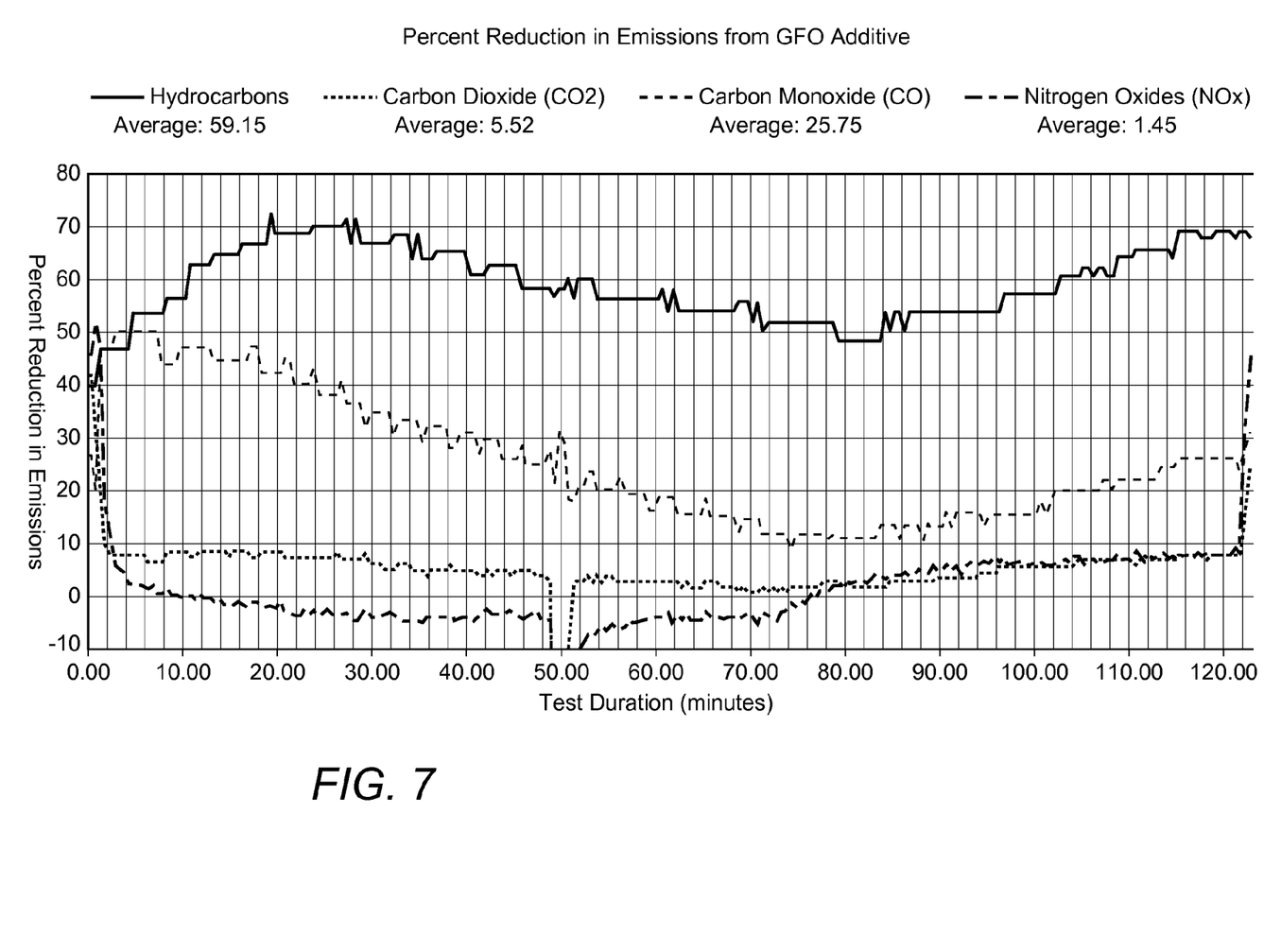
FIG. 7 shows the effect of canola treated by a method of the inventive concept on various air polluting emissions when used as a lubricating engine oil additive in a diesel engine.
Figure 8A:
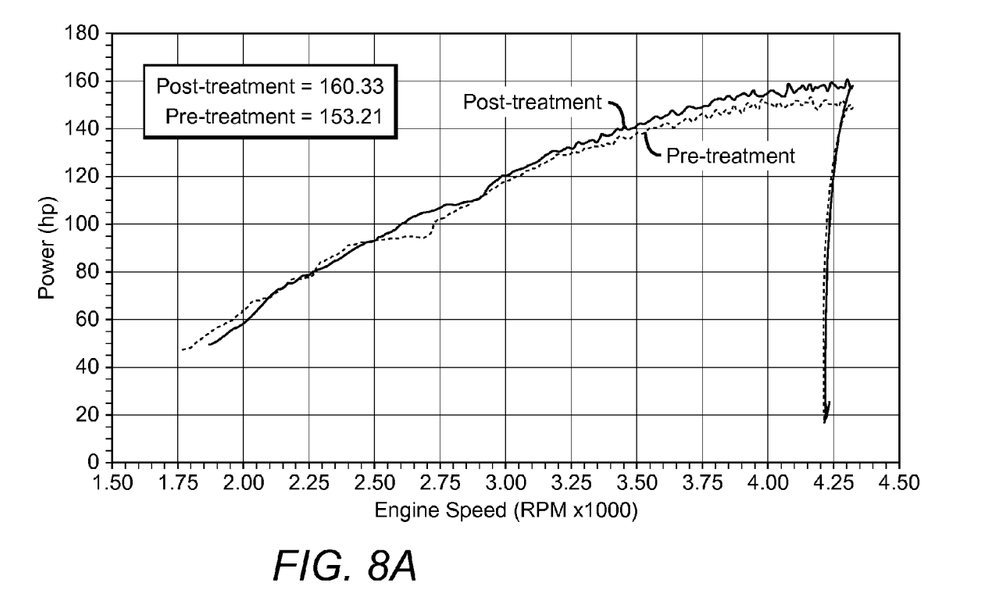
FIG. 8A and FIG. 8B show typical effects on engine power on use of an augmented engine oil of the inventive concept in a first high-mileage vehicle (FIG. 8A) and a second high-mileage vehicle (FIG. 8B).
Figure 8B:
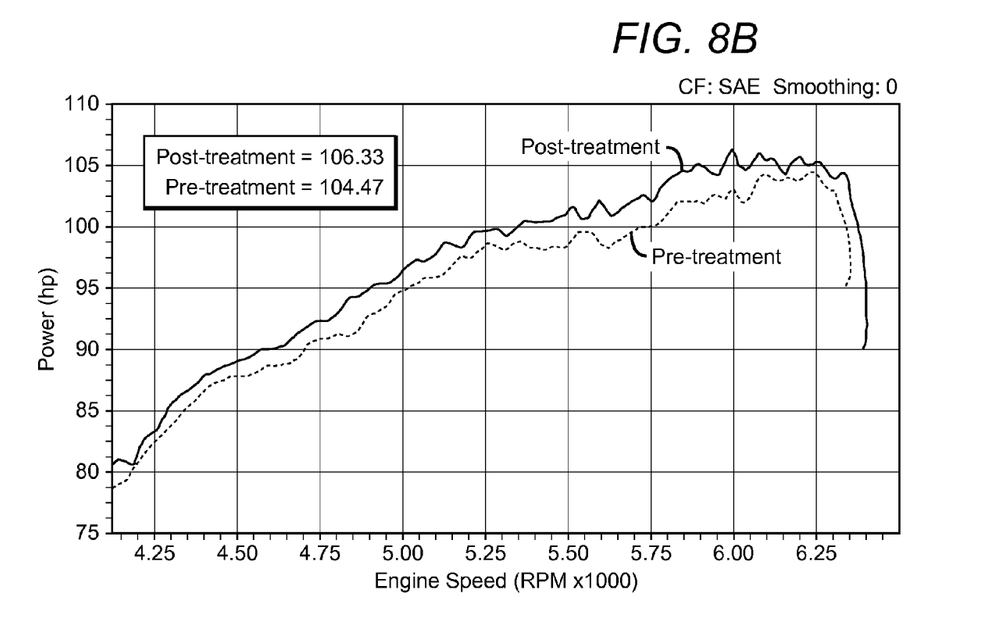

The effects of such an augmented motor oil on engine emissions is shown in FIG. 7 and in FIG. 8A and FIG. 8B. As shown in FIG. 7, hydrocarbon emissions were reduced by over 50%. Significant reductions in other major air pollutants and greenhouse gases (carbon monoxide, carbon dioxide, and nitrogen oxides) were also observed. As shown in FIG. 8A and FIG. 8B, improvements in engine performance (for example, high mileage engines) are also observed. Engine power output (in horsepower) over a range of engine speeds was characterized for a 1995 Ford Thunderbird with an accumulated mileage of over 279,000 miles (FIG. 8A) and for a 2005 Toyota Corolla with an accumulated mileage of over 130,000 miles (FIG. 8B), using both conventional motor oil and motor oil augmented by the addition of a modified vegetable oil of the inventive concept. Significant increases in engine output were observed over a range of engine speeds. In addition, owners reported noticeable reductions in engine noise and improvements in performance following the use of the augmented motor oil. Modified vegetable oils of the inventive concept can also be used as fuel additives, and in such applications can be added at 1% to 10% or more of the fuel volume.

Without wishing to be bound by theory, inventors believe that modified vegetable oils of the inventive concept produced by processes of the inventive concept contain oxygenated hydrocarbons, for example aldehydes, that are useful in breaking down, removing, and/or suspending the components of engine deposits. Similarly, the modified vegetable oil may act to improve the lubricating properties of the augmented engine oil. The resulting decrease in friction can lead to improved performance and greater engine output at lower rpms, decreasing emissions and improving mileage. Similar benefits can be realized by adding a modified vegetable oil of the inventive concept to a fuel to produce an augmented fuel for use in an internal combustion engine.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for producing a petroleum product additive, comprising:
    providing a vegetable oil;
    providing a first electrode and a second electrode; and,
    exposing at least a portion of the first electrode and at least a portion of the second electrode to the vegetable oil; and,
    applying an electrical potential to the first electrode and the second electrode, such that the electrical potential generated between the first electrode and the second electrode is of fixed polarity, wherein the potential is at least 3 kV; and
    introducing ozone to the vegetable oil as the electrical potential is applied.

2. The method of claim 1, wherein the ozone is applied at a rate of 0.1 to 10 grams per hour.

3. The method of claim 1, wherein the first electrode comprises a conductive material selected from the group consisting of copper, brass, stainless steel, conductive polymer, and graphite.

4. The method of claim 1, wherein the second electrode comprises a conductive material selected from the group consisting of copper, brass, stainless steel, conductive polymer, and graphite.

5. The method of claim 1, wherein the first electrode and the second electrode have the same composition.

6. The method of claim 1, wherein a gap is introduced between the first electrode and the second electrode, wherein the gap is from 5 mm to 100 mm.

7. The method of claim 6, wherein the gap is about 40 mm.

8. The method of claim 6, wherein the vegetable oil is exposed to the first electrode and the second electrode as a fluid flow directed through the gap.

9. The method of claim 1, wherein the vegetable oil is maintained between the first electrode and the second electrode for a period of 8 hours to 48 hours.

* * * * *